United States Patent [19]

Edwardson

[11] Patent Number: 4,834,653
[45] Date of Patent: May 30, 1989

[54] DENTAL INSTRUMENT
[75] Inventor: Svante R. Edwardson, Solna, Sweden
[73] Assignee: Dentatus International AB, Hagersten, Sweden
[21] Appl. No.: 186,467
[22] Filed: Apr. 26, 1988
[51] Int. Cl.$^4$ .............................................. A01C 5/02
[52] U.S. Cl. ....................................... 4/118; 433/122
[58] Field of Search ............... 433/133, 118, 122, 126, 433/127, 128

[56] References Cited

U.S. PATENT DOCUMENTS

| | | | |
|---|---|---|---|
| 2,791,835 | 5/1957 | Staunt | 433/128 |
| 3,552,022 | 1/1971 | Axelsson | 433/122 |
| 4,629,426 | 12/1986 | Levy | 433/118 |
| 4,773,855 | 9/1988 | Levy | 433/122 |

FOREIGN PATENT DOCUMENTS

WO82/03760  11/1982  World Int. Prop. O. .......... 433/118

OTHER PUBLICATIONS

"EVA Reciprocating Contra-Angle System" pamphlet, Dentatus AB, S-12653 Hagerstew, Sweden.

Primary Examiner—Robert Peshock
Attorney, Agent, or Firm—Young & Thompson

[57] ABSTRACT

A dental instrument is described by which a tooth file is automatically driven by a driver for producing alternating movement forces in the axial direction of a tool support bearing the file to a predetermined axial limit position in each direction, the distance between these limit positions being such that the instrument tool support is able to take an axial position in which it is unaffected by those movement forces. The movement forces affect the tool support only when it is moved from the unaffected axial position by an external force exerted on it and then by only the one of the forces acting in the axial direction opposite to the external force. External forces in each direction are able to move the tool support up to a predetermined maximum amplitude of action. Each movement force, besides having a first force component in the axial direction of the tool support, has also a second force component in an angular direction in order to impress also a rotational movement on the tool support when it is moved from that unaffected axial position.

6 Claims, 3 Drawing Sheets

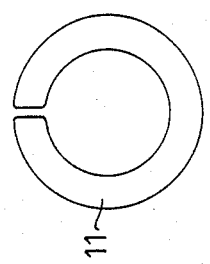
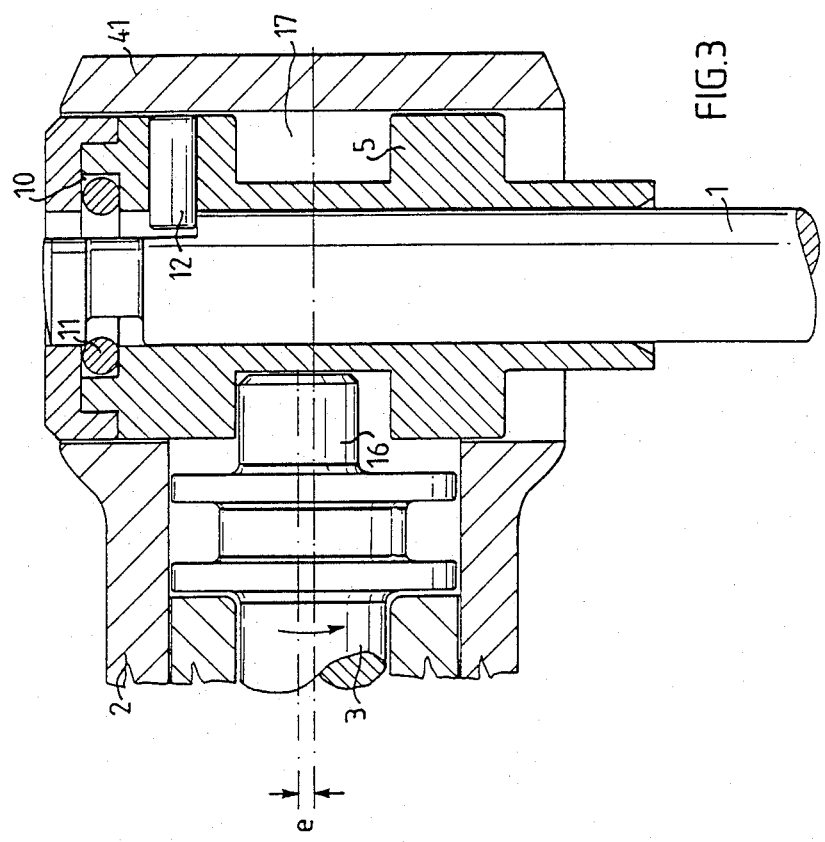

DENTAL INSTRUMENT

The present invention relates to a dental instrument and particularly to a motor driven tooth root canal treatment device.

BACKGROUND OF THE INVENTION

Tooth root canal treatment is usually made by hand by the dentist holding the rear end of a tooth root canal file between his forefinger and thumb and slightly rotating it to and fro while inserting it into the tooth and moving it down through the canal. However, there are also previously known automatically driven systems for treatment of the tooth root canals, but very few of them have been put on the market.

A previously known automatically driven system is discussed in U.S. Pat. No. 4,629,426 by Levy. The endodontic treatment instrument described by Levy includes a tooth root canal file inserted in a driving means, which vibrates the file in its axial direction while rotating it to and fro. The amplitude of the vibrations is maximum when the file does not meet any resistance and is reduced to a small value upon encountering an obstacle.

A disadvantage with this prior endodontic treatment instrument is that it is difficult to point the tip of the file exactly right into the opening in the tooth at insertion because of its vibration at maximum amplitude at that moment. It is also a disadvantage to have the minimum vibration amplitude just at an obstacle to get past.

It is an object of the present invention to provide a dental instrument, which does not vibrate when unloaded, i.e. when no part of it is placed in a tooth. In this way it will be easy to steer the tip of the instrument tool, such as a tooth file, exactly into a tooth root canal in a tooth.

It is another object of the invention to provide a dental instrument in which the instrument tool, such as a file, begins to rotate and vibrate as soon as it meets a resistance in axial direction.

It is a further object of the present invention to provide a dental instrument having its maximum vibration amplitude when meeting an obstacle in order to facilitate passage of the instrument tool.

These and other objects of the subject invention will become apparent from the description which follows and by reference to the attached drawings.

The invention is based upon a prior instrument described in the U.S. Pat. No. 3,552,022 owned by the same applicant. Changes have been made in this instrument in order to have the features aimed at above in order to make the inventive instrument.

DISCLOSURE OF THE INVENTION

The subject invention is a dental instrument including:
(a) a rotationally symmetrical tool support;
(b) a tool in the form of a tooth file;
(c) drive means for producing alternating movement forces in the direction of the axis of said tool support to a predetermined axial limit position from each direction, the distance between said limit positions being such that said tool support is able to take an axial position in which it is unaffected by said movement forces;
(d) said movement forces affecting said instrument tool support only when said instrument tool support is moved from said tool unaffected axial position by an external force exerted on said tool support and then by only the one of said forces acting in the axial direction opposite to said external force;
(e) external forces in each direction being able to move said tool support up to a predetermined maximum amplitude of action, and
(f) each said movement force besides having a first force component in the axial direction of said tool support also having a second force component in an angular an direction in order to impress also a rotational movement on said tool support when it is moved from said unaffected axial position.

BRIEF DESCRIPTION OF THE DRAWINGS

FIG. 3 is an enlarged sectional view of the instrument head of the embodiment shown in FIGS. 1 and 2.

FIG. 4 is a view of a lock ring shown in FIG. 3.

DESCRIPTION OF THE PREFERRED EMBODIMENT

Figures 1, 2:
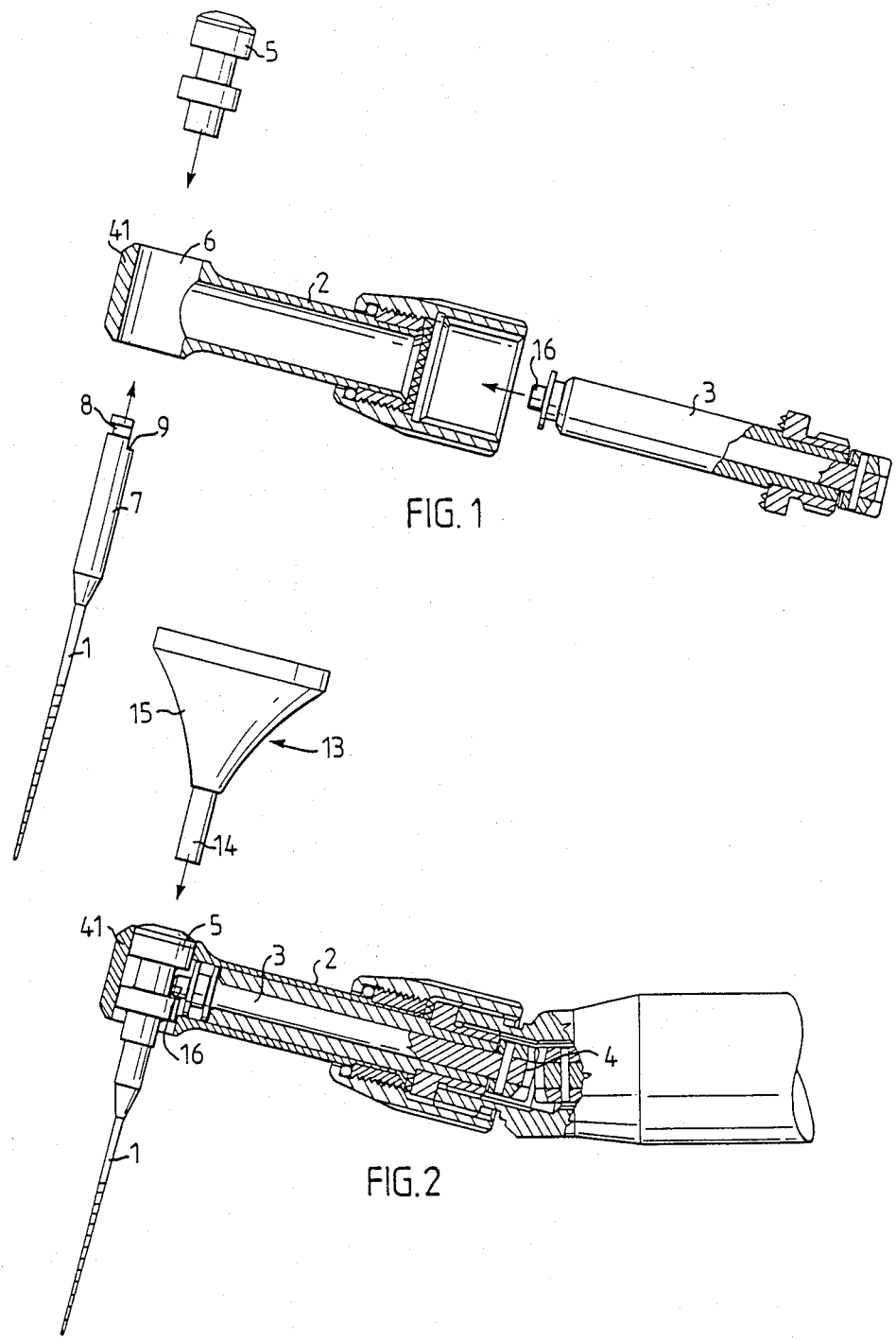
FIG. 1 is an exploded view, partly in section, of an embodiment according to the invention.
FIG. 2 is an assembled view, partly in section, of the embodiment shown in FIG. 1 and mounted on a rotational driving unit.

With reference to the Figures the apparatus for holding and driving an endodontic instrument tool 1, such as a tooth root canal file, during its operation comprises a slim generally cylindric handle 2 having a design general in the art. Said handle 2 houses a rotary shaft 3 which is driven by a motor (not shown) via a connection 4, as in dental hand pieces. Preferably the handle belongs to an already existing dental driving equipment, and merely an exchangeable end portion of the handle is designed according to the invention.

The handle ends with a cylindrical sleeve 41 set at right angles thereto and extending slightly therefrom at both sides. A piston-like socket 5 fits into a cylindrical bore 6 of the sleeve 41 and is guided thereby along a rectilinear path perpendicular to the length of the handle 2. A central cylindrical bore in the socket 5 is of a size suitable for inserting the shaft end portion of the tool 1.

A shaft end portion 7 has a circumferential groove 8 near its outer end. The shaft end portion 7 also has a straight cut-off part 9 parallel to its axis and extending inwardly past the groove 8 in the axial direction. With reference to FIG. 3 the socket 5 has a circumferential groove 10 in the wall of its cylindrical bore near one end of it adapted to house the outer end of the tool shaft end 7. An almost closed hold down spring ring 11 (FIg. 4) is inserted in the groove 10 such that it normally extends to some extend into the cylindrical bore and such that it is able to be pressed outwardly into the groove by the tool shaft end 7 when the tool is inserted into the bore. Thus, this spring ring 11 has an inner diameter less than the diameter of the bore and an outer diameter less than the outer diameter of the groove 10 but greater than the diameter of the bore. A stop pin 12 is inserted in a radial bore in the socket 5 near the groove 10 and extends into the bore a distance slightly less than the depth of the cut-off part 9 of the tool 1, such that it can rest in the part 9 of an inserted tool.

When the shaft end 7 of the tool 1 has moved past the spring ring 11 to such an extent that the spring ring is allowed to spring into the tool groove 8 further movement in that direction is prohibited by the end of the cut-off part 9 coming to rest on the stop pin 12. In this way the tool 9 is retained in the bore of the socket 5. It is to be understood that this kind of retaining feature may be provided also for other dental instrument tools than tooth files when inserted into an instrument tool support. It is also to be understood that the tool holding means described above is a preferred embodiment and that the tooth file may be held in the socket 5 in some other way.

A tool 13 having a cylindrical portion 14 adapted for insertion into the bore of the socket 5 and a wider portion 15 of a shape to be pressed upon by a finger is used to demount the tool 1 from the socket 5 by insertion into the bore.

The shaft 3 ends with an eccentric pin 16 which protrudes past the cylindrical wall of the bore 6 and into a circumferential groove 17 in the outer cylindrical wall of the socket 5.

In accordance with the invention the width of the groove 17 is such that the eccentric pin 16 is able to move inside the groove 17 when the shaft 3 is rotating without pushing the walls of the groove in any direction, thus having a full degree of freedom of rotation, provided that the socket takes a rest position. This means that if the distance between the eccentric axis and the axis of the shaft 3 is e (FIG. 3), then the width of the groove 17 is at least the diameter of the eccentric 16 plus 2e.

The distance e is for instance of the order of 0.25 mm so that the maximum amplitude of the eccentric movement will be of the order of 0.4 mm, but also other values of e may be used. There is a small play between the outside of the socket 5 and the bore wall 6 in order to have little friction therebetween.

When the shaft 3 is rotating with a frequency of about 50 to 60 strokes per second, as is common in dental instruments of this kind, and no external force is exerted on the tool, the socket 5 will remain in the rest position in which the eccentric 16 is freely rotating in the groove 17.

As soon as an external axial force is exerted onn the tool 1 the socket 5 is moved in one direction, and the eccentric 16 begins to run against one of the walls of the groove 17 giving it a push in the direction opposite the direction of the external force at each rotational turn. Then the tool 1 begins to rotate, since it is moved in an angular direction with each push by the eccentric moving in that angular direction during the push.

The tool 1 also begins to vibrate and with an amplitude which is greater the greater is the exerted external force up to a maximum amplitude. Since the eccentric 16 is able to push the socket 5 only at one of the walls of the groove 17 at each turn the maximum vibration amplitude is 2e (see FIG. 3).

It is to be noted that the tool 1 rotates always in the same direction as long as the external force is provided, but of course in one direction for an external force from one direction and in tfie opposite direction for an external force in the other direction, i.e. it will rotate in a different direction when moved down the root canal than when moved out of the canal.

Figure 6:
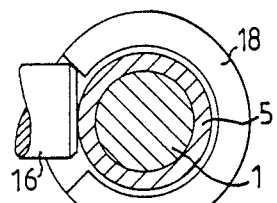
FIG. 6 is a sectional view along line VI—VI of the socket shown in FIG. 5.
Figure 5:
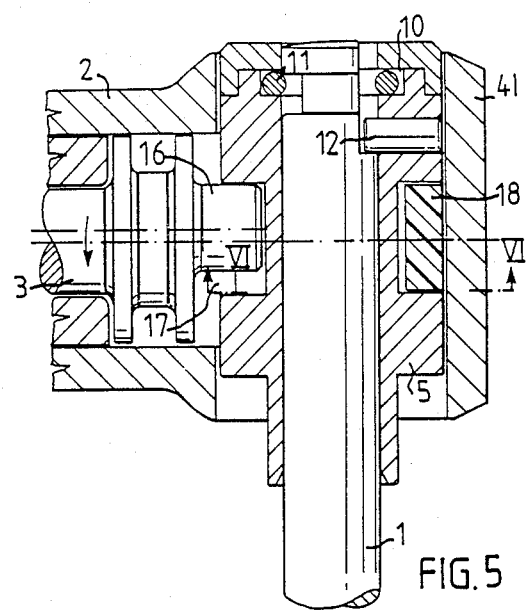
FIG. 5 is a sectional view of the instrument head of a second embodiment according to the invention.

The socket 5, in the embodiment shown in FIG. 3, may have a tendency to vibrate even when the socket 5 is in its rest position because of the low friction between the socket 5 and the inner wall of the sleeve 4 and because the weight of the tool 1 will give a slight force in the axial direction. This could be avoided by placing a plastic ring 18 having a sector removed for a length sufficient to allow freedom of rotation of the eccentric 16 within the sector, as is apparent from FIGS. 5 and 6. The plastic ring 18 has a very slight friction on the wall of the cylindrical bore 6 but not on the inner wall of the groove 17. The friction on the cylindrical bore 6 should be just enough to compensate for the effect of the weight of the tool 1, so that the socket 5 will stay in said rest position always when the instrument is unloaded, i.e. not inserted in a tooth.

Figure 8:
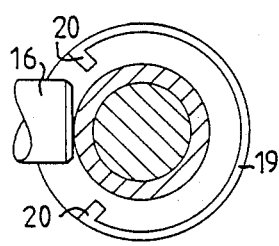
FIG. 8 is a sectional view along line VIII—VIII of the socket shown in FIG. 7.
Figure 7:
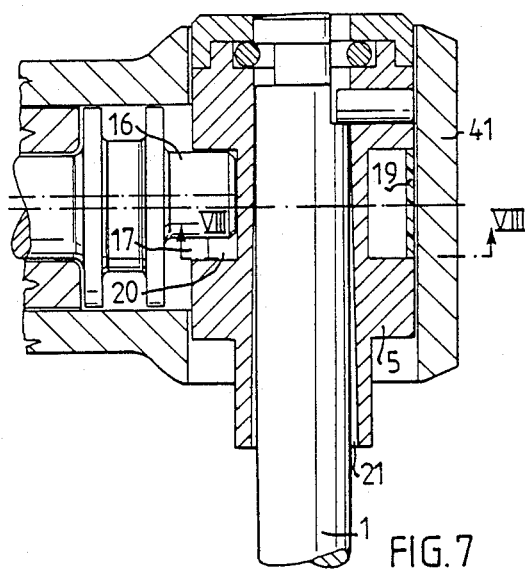
FIG. 7 is a sectional view of the instrument head of a third embodiment according to the invention.

FIGS. 7 and 8 show a second embodiment of a means to prevent unwanted axial movement. A spring clamp in the form of a non locked ring 19 having an outer diameter approximately corresponding to the bore in the socket 5 and inwardly bent ends 20 having such distance from each other that the eccenter 16 has a full freedom of rotation therebetween. The friction between the ring 19 and the walls of the socket bore is chosen to be just enough to prevent possible vibration of the tool caused by the influence of the weight of the tool and is thus very slight.

FIG. 7 also shows an embodiment in which the socket 5 has a slightly conical bore 21, in which the tool 1 is inserted. The bore 21 has its wider part toward the operational part of the tool 1. In this way the tool 1 is able to move laterally to some extent when a lateral force is provided on its operational part by the wall of the tooth root canal in order to facilitate the path finding of the tool when moved down the tooth root canal. Instead of having a slightly conical socket bore the tool shaft end 7 may be slightly conical having the tapered part of the shaft turned to the file end of the tool.

While there have been shown and described what are considered at present to be the preferred embodiments of the present invention, it will be appreciated by those skilled in the art that modifications of such embodiments may be made. It is therefore desired that the invention not be limited to these embodiments, and it is intended to cover in the appended claims all such modifications as fall within the true spirit and scope of the invention. It is to be noted that other tooth files than tooth root canal files may be used with the inventive instrument.

I claim:

1. A dental instrument including:
   (a) a tool support;
   (b) a tool in the form of a tooth file carried by said support;
   (c) drive means for producing alternating movement forces in the direction of the axis of said tool support to a predetermined axial limit position from each direction, the distance between said limit positions being such that said instrument tool support is able to take an axial position in which it is unaffected by said movement forces;
   (d) said movement forces affecting said tool support only when said tool support is moved from said unaffected axial position by an external force exerted on said tool support and then by only the one of said forces acting in the axial direction opposite to said external force;

(e) external forces in each direction being able to move said tool support up to a predetermined maximum amplitude of action, and (f) each said movement force besides having a first force component in the axial direction of said tool support also having a second force component in an angular direction in order to impress also a rotational movement on said tool support when it is moved from said unaffected axial position.

2. An instrument according to claim 1, wherein said drive means includes an eccentric provided at the end of a rotation axis directed essentially perpendicular to said tool support, said support having a circumferential groove into which said eccentric protrudes, said groove having a width sufficient to allow freedom of rotation of said eccentric when said instrument tool support is at its unaffected axial position.

3. An instrument according to claim 1 characterized by a means providing a slight frictional resistance to axial movement of said tool support.

4. An instrument according to claim 3, wherein said frictional resistance means is inserted in said groove.

5. An instrument according to claim 1, wherein an axial bore provided in said tool support to receive said tool is slightly conical having its wider part toward the operational part of said tool.

6. A dental instrument as claimed in claim 1, further including:

(a) an axially extending bore in said tool support to receive a tool;

(b) said drive means driving said support;

(c) said tool having a shaft end portion disposed in said bore in said support;

(d) a circumferential groove in said shaft end portion;

(e) a circumferential groove in one end of said bore in said support adapted to be situated opposite to said groove in said shaft end portion;

(f) an almost closed spring ring inserted in said groove in said bore, said spring ring having an inner diameter less than the diameter of said bore and an outer diameter less than the outer diameter of said groove in said bore but greater than the diameter of said bore;

(g) a cut-away portion of said shaft end portion of said tool extending from its rear end a distance past said groove; and (h) stop means extending into said bore adapted to rest in said cut-away portion of said tool near its inner end when said tool is placed in a position having its groove in front of said groove in said bore.

* * * * *